US010863929B2

(12) United States Patent
Yamada

(10) Patent No.: US 10,863,929 B2
(45) Date of Patent: Dec. 15, 2020

(54) STEP COUNT MEASURING APPARATUS AND MEDIUM

(71) Applicant: ALPS ALPINE CO., LTD., Tokyo (JP)

(72) Inventor: Yukimitsu Yamada, Miyagi (JP)

(73) Assignee: ALPS ALPINE CO., LTD., Tokyo (JP)

( * ) Notice: Subject to any disclaimer, the term of this patent is extended or adjusted under 35 U.S.C. 154(b) by 327 days.

(21) Appl. No.: 15/922,057

(22) Filed: Mar. 15, 2018

(65) Prior Publication Data

US 2018/0199858 A1  Jul. 19, 2018

Related U.S. Application Data

(63) Continuation of application No. PCT/JP2016/079818, filed on Oct. 6, 2016.

(30) Foreign Application Priority Data

Oct. 15, 2015 (JP) ................................. 2015-203394

(51) Int. Cl.
*G01C 21/10* (2006.01)
*A61B 5/11* (2006.01)
(Continued)

(52) U.S. Cl.
CPC ............ *A61B 5/1123* (2013.01); *A61B 5/112* (2013.01); *A61B 5/1118* (2013.01);
(Continued)

(58) Field of Classification Search
CPC ..... A61B 5/1123; A61B 5/1118; A61B 5/112; A61B 5/6803; A61B 2562/0219; G01C 22/006; G06M 1/108
See application file for complete search history.

(56) References Cited

U.S. PATENT DOCUMENTS

2009/0319221 A1* 12/2009 Kahn ................... A61B 5/1123
702/141
2011/0004440 A1  1/2011 Asada et al.
(Continued)

FOREIGN PATENT DOCUMENTS

EP          1770368         4/2007
JP        2002-360549      12/2002
(Continued)

OTHER PUBLICATIONS

Extended European Search Report for 16855343.6 dated Oct. 5, 2018.
(Continued)

*Primary Examiner* — Mohamed Charioui
*Assistant Examiner* — Christine Y Liao
(74) *Attorney, Agent, or Firm* — IPUSA, PLLC

(57) ABSTRACT

A step count measuring apparatus that measures the step count based on a degree of acceleration is provided. The step count measuring apparatus includes a local maximum/minimum value detection unit configured to detect at least one of a local maximum value and a local minimum value of the acceleration during a predetermined time, a threshold value determination unit configured to determine a threshold value based on at least one of the local maximum value and the local minimum value detected by the local maximum/minimum value detection unit, and a step count measuring unit configured to measure the step count based on the acceleration and the threshold value that has been determined by the threshold value determination unit.

6 Claims, 6 Drawing Sheets

(51) Int. Cl.
 *A61B 5/00*   (2006.01)
 *G06M 1/10*   (2006.01)
 *G01C 22/00*  (2006.01)

(52) U.S. Cl.
 CPC .......... *A61B 5/6803* (2013.01); *G01C 22/006* (2013.01); *G06M 1/108* (2013.01); *A61B 2562/0219* (2013.01)

(56) References Cited

U.S. PATENT DOCUMENTS

| | | |
|---|---|---|
| 2012/0291544 A1 | 11/2012 | Kawabe |
| 2015/0127290 A1 | 5/2015 | Plasterer et al. |
| 2015/0198460 A1 | 7/2015 | Yamato et al. |
| 2015/0366739 A1 | 12/2015 | Endo |

FOREIGN PATENT DOCUMENTS

| | | |
|---|---|---|
| JP | 2009-223744 | 10/2009 |
| JP | 2011-200390 | 10/2011 |
| JP | 6017062 | 9/2012 |
| JP | 2015-133072 | 7/2015 |
| JP | 5758028 | 8/2015 |
| WO | 2015/101567 | 7/2015 |

OTHER PUBLICATIONS

International Search Report dated Dec. 27, 2016 in PCT/JP2016/079818 filed on Oct. 6, 2016.

\* cited by examiner

STEP COUNT MEASURING APPARATUS AND MEDIUM

CROSS-REFERENCE TO RELATED APPLICATIONS

The present application is a continuation application of International Application No. PCT/JP2016/079818 filed on Oct. 6, 2016, which claims priority to Japanese Patent Application No. 2015-203394 filed on Oct. 15, 2015. The contents of these applications are incorporated herein by reference in their entirety.

BACKGROUND OF THE INVENTION

1. Field of the Invention

The present invention relates to a step count measuring apparatus and a computer readable recording medium that includes a step count measuring program used for measuring a step count (counting the number of steps) while walking and a step count while running.

2. Description of the Related Art

A conventional pedometer detects the acceleration in an up-and-down direction (vertical direction) of a person walking by using an acceleration sensor, and measures the number of steps based on changes in the detected values. Specifically, the pedometer measures the number of steps by determining that the walker has walked a step every time when the detected value of the acceleration exceeds a predetermined threshold value. However, there is a case in which multiple acceleration peaks appear while walking one step due to an irregular movement of the person walking, and the pedometer determines that the walker has walked multiple steps.

With respect to the above, in Patent Document 1, when measuring the number of steps based on the degree of the acceleration output from the acceleration sensor, it is proposed to detect a lower limit peak value at which the acceleration switches from a decreasing state to an increasing state, to detect an upper limit peak value at which the acceleration switched from an increasing state to a decreasing state, and to measure the number of steps based on the lower limit peak value and the upper limit peak value.

CITATION LIST

Patent Document

[Patent Document 1] Japanese Patent No. 5017062

SUMMARY OF THE INVENTION

Technical Problem

However, in the step count measurement proposed in the conventional technology, a single threshold value is used for measuring the step count. In other words, the same threshold value is used regardless of the state whether walking or running. As a result, there is a disadvantage that the number of steps while walking may be accurately measured but the number of steps while running cannot be accurately measured, or that the number of steps while running may be accurately measured but the number of steps while walking cannot be accurately measured.

In view of the above, the present invention has been made. An object of the present invention is to provide a step count measuring apparatus and a step count measuring that can accurately measure the number of steps while walking and while running.

Solution to Problem

A step count measuring apparatus that measures the number of steps based on acceleration according to an embodiment of the present invention is provided. The step count measuring apparatus includes a local maximum/minimum value detection unit configured to detect at least one of a local maximum value and a local minimum value of the acceleration during a predetermined time period, a threshold value determination unit configured to determine a threshold value based on at least one of the local maximum value and the local minimum value detected by the local maximum/minimum value detection unit, and a step count measuring unit configured to measure the number of steps based on the acceleration and the threshold value determined by the threshold value determination unit.

According to the above-described arrangement, a threshold value that is appropriate for the moving state is determined based on at least one of the local maximum value and the local minimum value of the acceleration detected by the local maximum/minimum value detection unit, and the number of steps is measured based on the determined threshold value. Therefore, the number of steps while walking and the number of steps while running can be accurately measured by using the threshold values appropriate for the corresponding moving states.

Preferably, in an embodiment of the present invention, the threshold value determination unit determines, as the threshold value, a first threshold value in the case where at least one of the local maximum value and the local minimum value exceeds a predetermined value, and determines, as the threshold value, a second threshold value that is less than the first threshold value in the case where at least one of the local maximum value and the local minimum value is equal to or less than the predetermined value.

According to the above-described arrangement, the first threshold value is determined as the threshold value in the case where at least one of the local maximum value and the local minimum value exceeds the predetermined value (in the case of running), and the second threshold value that is less than the first threshold value is determined as the threshold value in the case where at least one of the local maximum value and the local minimum value is equal to or less than the predetermined value (in the case of walking). Therefore, the number of steps while walking and the number of steps while running can be measured more accurately.

Preferably, in an embodiment of the present invention, the threshold value determination unit determines the threshold value after the local maximum value and the local minimum value have been both detected by the local maximum/minimum value detection unit.

According to the above-described arrangement, the threshold value determination unit determines the threshold value after the local maximum value and the local minimum value have been both detected by the local maximum/minimum value detection unit. Therefore, the number of steps while walking and the number of steps while running can be measured furthermore accurately.

Preferably, in an embodiment of the present invention, the threshold value determination unit determines the threshold value after one of the local maximum value and the local minimum value has been detected by the local maximum/minimum value detection unit.

According to the above-described arrangement, the threshold value determination unit determines the threshold value after one of the local maximum value and the local minimum value has been detected by the local maximum/minimum value detection unit. Therefore, compared with a case in which the threshold value is determined after the local maximum value and the local minimum value have been both detected, it is possible to determine the threshold value in a shorter time.

Preferably, in an embodiment of the present invention, the local maximum/minimum value detection unit detects the local maximum value and the local minimum value, and the step count measuring unit measures the number of steps based on a difference between the local maximum value and the local minimum value detected by the local maximum/minimum value detection unit.

According to the above-described arrangement, the local maximum/minimum value detection unit detects the local maximum value and the local minimum value, and the step count measuring unit measures the number of steps based on a difference between the local maximum value and the local minimum value detected by the local maximum/minimum value detection unit. Therefore, the number of steps can be measured more accurately.

Preferably, in an embodiment of the present invention, the acceleration that is input to the local maximum/minimum value detection unit is a sum of the squares of acceleration values in three axis directions including an X axis, a Y axis, and a Z axis that are orthogonal to each other.

According to the above-described arrangement, the acceleration that is input to the acceleration that is input to the local maximum/minimum value detection unit is a sum of the squares of acceleration values in three axis directions including an X axis, a Y axis, and a Z axis that are orthogonal to each other. Therefore, compared with a case of using only acceleration values in one axis direction or acceleration values in two axis directions, movement of the user's body can be determined more accurately. As a result, it is possible to measure the number of steps more accurately.

Preferably, in an embodiment of the present invention, an acceleration sensor that measures the acceleration is included.

According to the above-described arrangement, an acceleration sensor that measures the acceleration is included. Therefore, it is not necessary to include a separate acceleration sensor. Further, compared with a gyro sensor, the power consumption is less. Therefore, the above-described arrangement is preferable for a wearable device or a mobile device that is driven by an internal power supply such as a storage battery.

A computer readable recording medium that includes a step count measuring program that measures the number of steps based on acceleration according to an embodiment of the present invention is provided. The step count measuring program causes a computer to perform detecting at least one of a local maximum value and a local minimum value of the acceleration during a predetermined time period, determining a threshold value based on at least one of the local maximum value and the local minimum value detected by the detecting, and measuring the number of steps based on the acceleration and the threshold value determined by the determining.

According to the above-described program, a computer is caused to perform detecting at least one of a local maximum value and a local minimum value of the acceleration during a predetermined time period, determining a threshold value based on the at least one of the local maximum value and the local minimum value detected by the detecting, and measuring the number of steps based on the acceleration and the determined threshold value. Therefore, it is possible to accurately measure the number of steps while walking and the number of steps while running.

Advantageous Effects of Invention

With a step count measuring program according to an embodiment of the present invention, it is possible to accurately measure the number of steps while walking and the number of steps while running.

DETAILED DESCRIPTION OF THE PREFERRED EMBODIMENTS

A step count measuring apparatus according to an embodiment of the present invention is, for example, a wearable device of a headphone type, a glasses type, a watch type, or a bracelet type, that is used by being attached to (being worn on) the body of a user.

In the following descriptions, one or more embodiments of the present invention will be described by using a wearable device of a headphone type as an example. It should be noted that a step count measuring apparatus according to an embodiment of the present invention may be installed in a mobile device (mobile apparatus) such as a pedometer, a mobile phone, a smart-phone, etc.

First Embodiment

Figure 1:
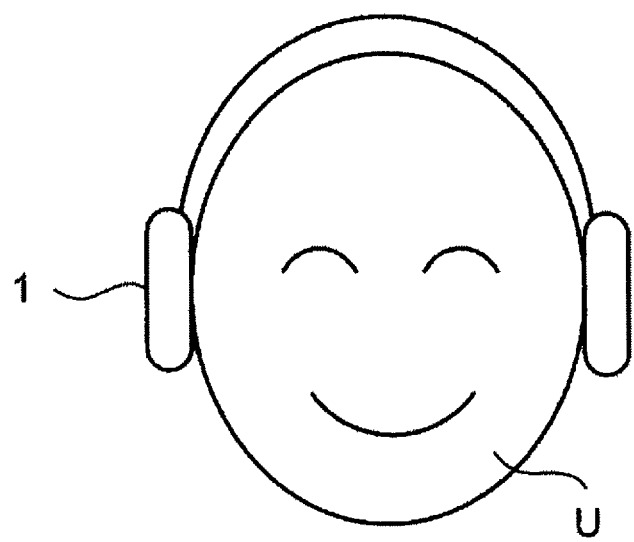
FIG. 1 is an overview of a step count measuring apparatus according to a first embodiment of the present invention.

FIG. 1 is an overview of a step count measuring apparatus 1 according to a first embodiment of the present invention. As described above, the step count measuring apparatus 1 is a wearable device of a headphone type, and is implemented in a headphone. A user (hereinafter, referred to as a "user U") uses the step count measuring apparatus 1 illustrated in FIG. 1 by attaching it to the head.

(Structure of Step Count Measuring Apparatus 1)

Figure 2:
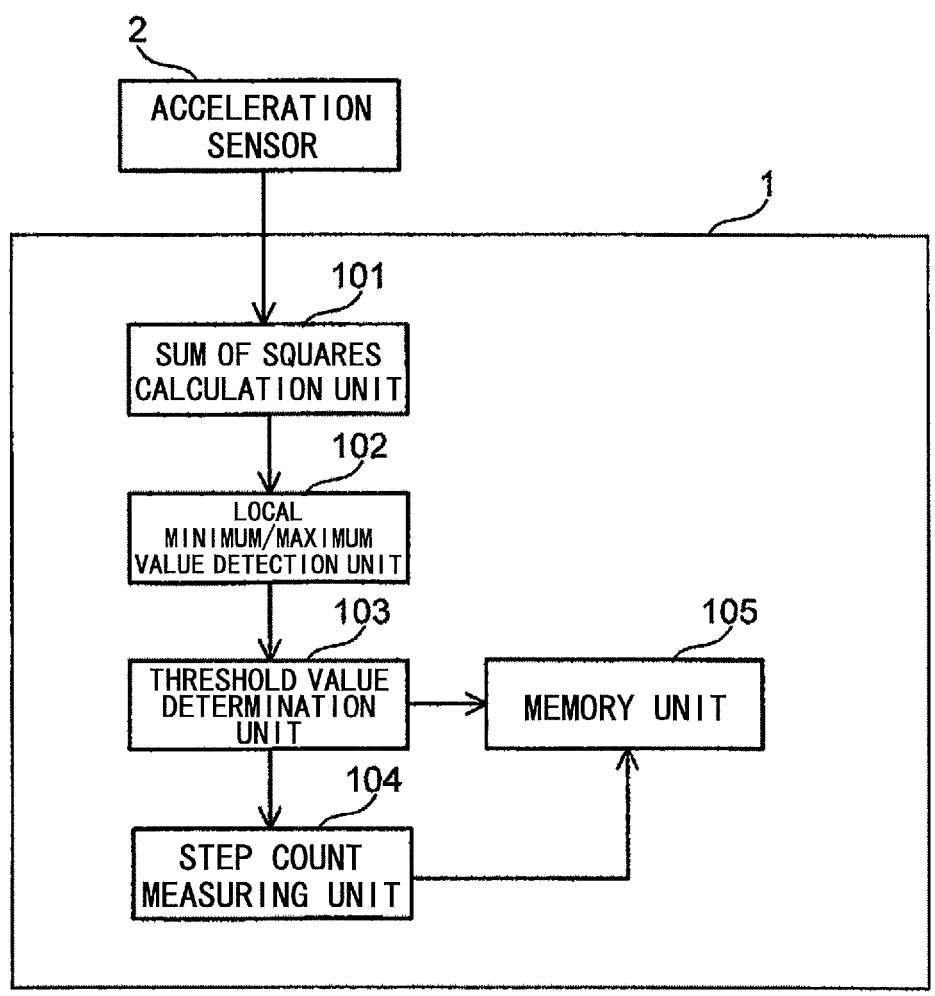
FIG. 2 is a functional block diagram of a step count measuring apparatus according to a first embodiment of the present invention.

FIG. 2 is a functional block diagram of a step count measuring apparatus according to a first embodiment of the present invention, in which a memory element, a CPU, etc., are included. The step count measuring apparatus 1 includes a sum of squares calculation unit 101, a local maximum/minimum value detection unit 102, a threshold value determination unit 103, a step count measuring unit 104, and a memory unit 105. Functions of the step count measuring apparatus 1 illustrated in FIG. 2 may be realized by hardware, or may be realized by a processor such as a CPU (Central Processing Unit) that executes a step count measuring program. The above step count measuring program is a step count measuring program according to an embodiment of the present invention.

Further, as illustrated in FIG. 2, a step count measuring apparatus 1 according to a first embodiment of the present invention is connected to an acceleration sensor 2 via wireless connection or wired connection, and receives acceleration data from the acceleration sensor 2. Here, the acceleration sensor 2 measures real-time acceleration data in three axis directions including an X axis, a Y axis, and a Z axis that are orthogonal to each other, and sequentially outputs the measured data.

In a first embodiment of the present invention, it is assumed that the X axis is related to an acceleration measurement in a left-and-right direction with respect to the user U, the Y axis is related to an acceleration measurement in a front-and-back direction with respect to the user U, and the Z axis is related to an acceleration measurement in a vertical direction with respect to the user U. It should be noted that the acceleration sensor 2 may be included in a step count measuring apparatus 1 according to the first embodiment.

The sum of squares calculation unit 101 performs sampling of analog voltage signals of the X axis, the Y axis, and the Z axis, that are output from the acceleration sensor 2 at a predetermined sampling period, and converts the sampled signals into digital data. It should be noted that, in order to prevent a malfunction caused by the sample timing deviation, the sampling of the analog voltage signals is performed substantially at the same time with respect to the X axis, the Y axis, and the Z axis. It should be noted that the acceleration sensor 2 may generate digital signals that indicate respective voltages with respect to the X axis, the Y axis, and the Z axis.

The sum of squares calculation unit 101 calculates the square root w of the sum of the squares of acceleration values in the X axis, the Y axis, and the Z axis that have been converted to the digital data.

Specifically, the square root w of the sum of squares is calculated by using the following formula (1).

(Math 1)

$$w=(x^2+y^2+z^2)^{1/2} \quad (1)$$

x: acceleration in the X axis
y: acceleration in the Y axis
z: acceleration in the Z axis
w: square root of a sum of the squares The sum of squares calculation unit 101 sequentially outputs the calculated square roots of the sum of squares of acceleration values in the X axis, the Y axis, and the Z axis. It should be noted that, in the first embodiment, the square root of the sum of the squares is calculated directly from the sampled acceleration values in the X axis, the Y axis, and the Z axis. However, the square root of the sum of the squares may be calculated from moving average values of the sampled acceleration values in the X axis, the Y axis, and the Z axis.

The local maximum/minimum value detection unit 102 performs sampling of the values output from the sum of squares calculation unit 101 during a predetermined time, and detects a local maximum value (the largest value) and a local minimum value (the smallest value) from the sampled values during the predetermined time. Specifically, after detecting the local minimum value at first, the local maximum/minimum value detection unit 102 detects the local maximum value in a state in which the detected local minimum value is retained. It should be noted that the predetermined time described in an embodiment of the present invention is a time during which the user walks one step or runs one step (e.g., 500 ms).

The threshold value determination unit 103 determines whether the local maximum value detected by the local maximum/minimum value detection unit 102 exceeds a predetermined value A. In the case where the local maximum value detected by the local maximum/minimum value detection unit 102 exceeds the predetermined value A, the threshold value determination unit 103 determines that the user is running, and determines a threshold value B (first threshold value) as a threshold value to be used. Further, in the case where the local maximum value detected by the local maximum/minimum value detection unit 102 is equal to or less than the predetermined value A, the threshold value determination unit 103 determines that the user is walking, and determines a threshold value C (second threshold value) that is less than the threshold value B (first threshold value) as the threshold value to be used. The predetermined value A is determined in advance based on the values of the square roots of the sum of the squares of the actual acceleration values while running and while walking. Further, the predetermined threshold value B is determined in advance based on the values of the square roots of the sum of the squares of the actual acceleration values while running and the step counts at that time. Further, the predetermined threshold value C is determined in advance based on the values of the square roots of the sum of the squares of the actual acceleration values while walking and the actual step counts.

Figure 3:
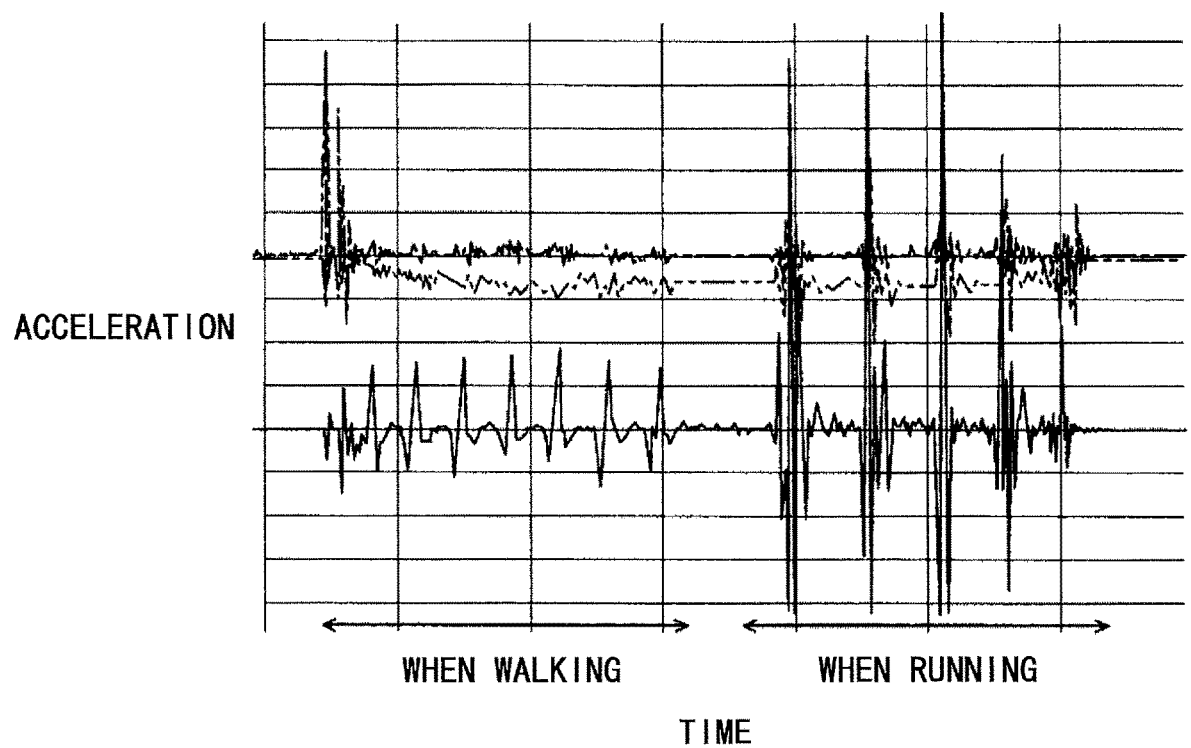
FIG. 3 is a drawing illustrating threshold value determination by a step count measuring apparatus according to a first embodiment of the present invention.
Figure 4:
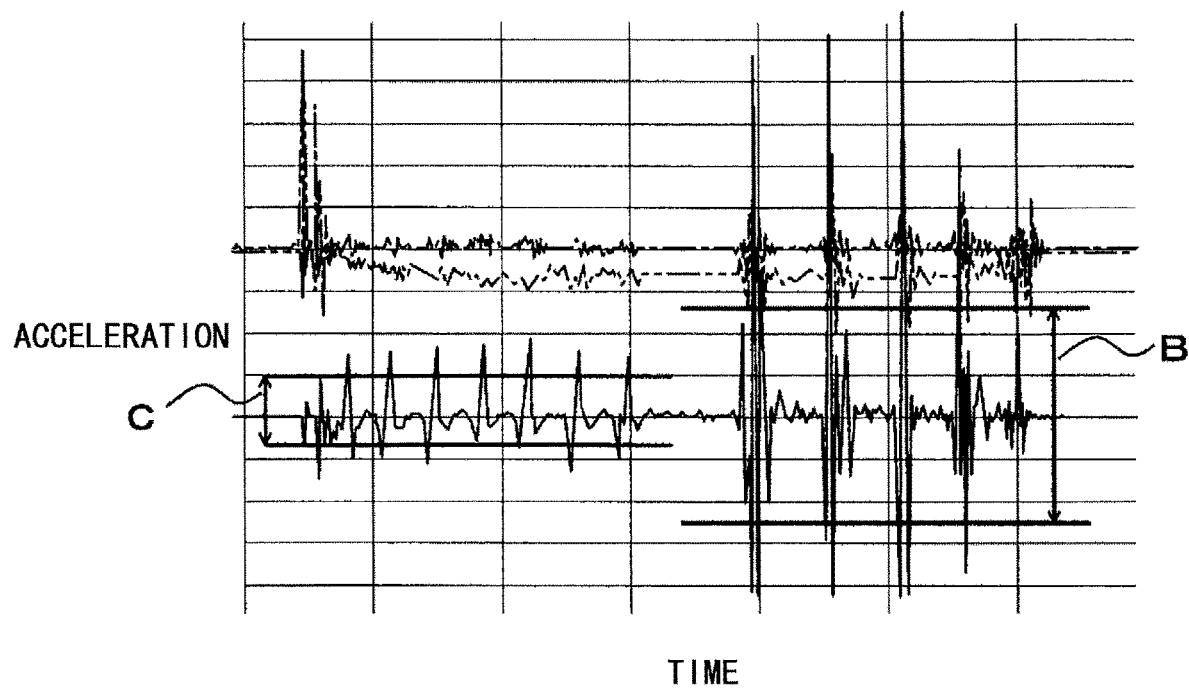
FIG. 4 is a drawing illustrating threshold value determination by a step count measuring apparatus according to a first embodiment of the present invention.

FIG. 3 and FIG. 4 are drawings illustrating the reason for changing the threshold value. The vertical axis in FIG. 3 and FIG. 4 represents the degree of the acceleration. The horizontal axis in FIG. 3 and FIG. 4 represents time. Further, a one-dot chain line in FIG. 3 and FIG. 4 represents acceleration in the Y axis direction, a two-dot chain line represents acceleration in the X axis direction, and a solid line represents acceleration in the Z axis direction.

Here, in FIG. 3 and FIG. 4, the acceleration change while walking is illustrated on the left side, and the acceleration change while running is illustrated on the right side. As illustrated in FIG. 3 and FIG. 4, the measured degree of the acceleration while walking is quite different from the measured degree of the acceleration while running. Therefore, as illustrated in FIG. 3, if the threshold value for measuring the step count is fixed to the threshold value for walking, then there is a risk of false detection of the step count when the user is running (when the acceleration changes greatly). For example, there is a risk of the degree of the acceleration exceeding the threshold value multiple times during a time the user runs one step, and thus, there is a risk that, for a single actual step, a plurality of steps may be erroneously measured.

Further, if the threshold value for measuring the step count is fixed to the threshold value while running, then there is a risk of false step count detection when the user is walking (when the acceleration changes slightly). For example, there is a risk of the degree of the acceleration not exceeding the threshold value in spite of the fact that the user has walked multiple steps, and thus, there is a risk that, for a plurality of actual steps, no step may be measured.

Therefore, in the first embodiment, as illustrated in FIG. 4, different threshold values are used depending on whether the user is walking or running. As a result, it is possible to reduce the possibility of the false detection in which the measured step count is erroneously detected as plural in spite of the fact that the actual step count is one.

The step count measuring unit 104 measures the step count based on the acceleration and the threshold value that is determined by the threshold value determination unit 103. Specifically, after calculating the difference between the local maximum value and the local minimum value that are detected by the local maximum/minimum value detection unit 102, in the case of the difference exceeding the threshold value that has been determined by the threshold value determination unit 103, one step is measured (counted) by the step count measuring unit 104, and in the case of the difference being equal to or less than the threshold value that has been determined by the threshold value determination unit 103, no step is measured (counted) by the step count measuring unit 104.

The predetermined value A that is used by the threshold value determination unit 103 and the threshold values B and C that are used by the step count measuring unit 104 are stored in the memory unit 105.

(Operations of Step Count Measuring Apparatus 1)

Figure 5:
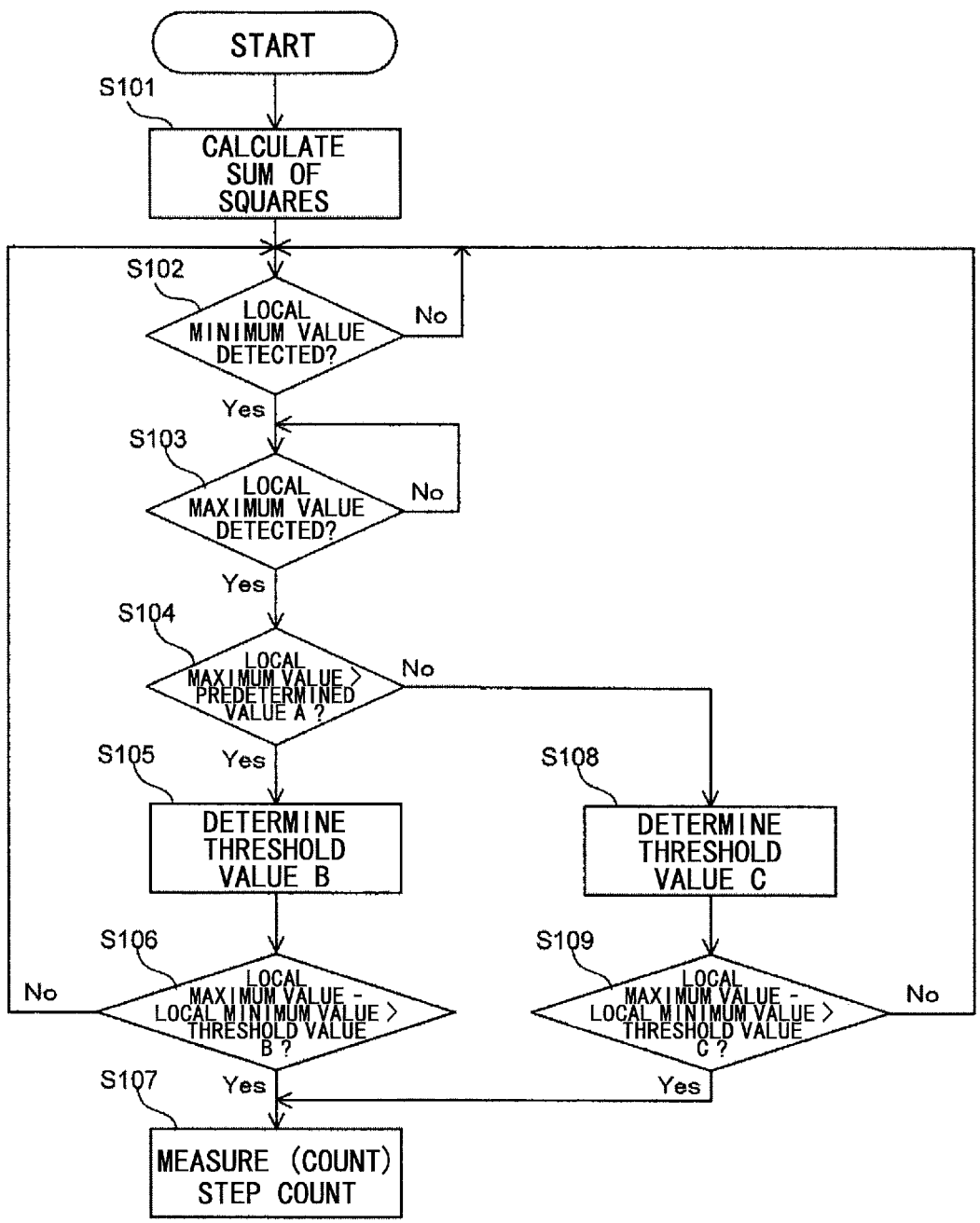
FIG. 5 is a flowchart illustrating operations of a step count measuring apparatus according to a first embodiment of the present invention.

FIG. 5 is a flowchart illustrating operations of a step count measuring apparatus 1 according to the first embodiment. In the following, referring to FIG. 1 through FIG. 5, operations of the step count measuring apparatus 1 according to the first embodiment will be described.

At first, after sampling the analog voltage signals in the X axis, Y axis, and Z axis, that have been output from the acceleration sensor 2 at a predetermined sampling period, and converting the sampled analog voltage signals into digital data, the sum of squares calculation unit 101 calculates the square root w of the sum of the squares of the respective acceleration values in the X axis, Y axis, and Z axis that have been converted to the digital data (S101).

Next, the local maximum/minimum value detection unit 102 performs sampling of the values that have been output from the sum of squares calculation unit 101 during a predetermined time, and detects a local minimum value (the smallest value) from the sampled values during the predetermined time (S102). Next, the local maximum/minimum value detection unit 102 detects a local maximum value (the largest value) in a state in which the detected local minimum value is retained (S103).

Next, the threshold value determination unit 103 determines whether the local maximum value detected by the local maximum/minimum value detection unit 102 exceeds a predetermined value A (S104). In the case where the local maximum value detected by the local maximum/minimum value detection unit 102 exceeds the predetermined value A, the threshold value determination unit 103 determines that the user is running, and determines a threshold value B (first threshold value) as a threshold value to be used (S105).

After calculating a difference between the local maximum value and the local minimum value that have been detected by the local maximum/minimum value detection unit 102, the step count measuring unit 104 determines whether the difference exceeds the threshold value B that has been determined by the threshold value determination unit 103 in step S105 (S106). In the case of the difference exceeding the threshold value B (Yes in S106), one step is measured by the step count measuring unit 104 (S107). Further, in the case where the difference does not exceed the threshold value B (No in S106), no step is measured by the step count measuring unit 104.

Further, in the case where the local maximum value detected by the local maximum/minimum value detection unit 102 does not exceed the predetermined value A (No in S104), the threshold value determination unit 103 determines that the user is walking, and determines a threshold value C (second threshold value) as the threshold value to be used (S108).

After calculating a difference between the local maximum value and the local minimum value that have been detected by the local maximum/minimum value detection unit 102, the step count measuring unit 104 determines whether the difference exceeds the threshold value C that has been determined by the threshold value determination unit 103 in step S108 (S109). In the case of the difference exceeding the threshold value C (Yes in S109), one step is measured by the step count measuring unit 104 (S107). Further, in the case of the difference not exceeding the threshold value C (No in S109), no step is measured by the step count measuring unit 104.

As described above, a step count measuring apparatus 1 is provided according to an embodiment of the present invention measures the step count based on the degree of acceleration. The step count measuring apparatus includes a local maximum/minimum value detection unit 102 configured to detect a local maximum value and a local minimum value of the acceleration during a predetermined time, a threshold value determination unit 103 configured to determine a threshold value based on the local maximum value and the local minimum value detected by the local maximum/minimum value detection unit 102, and a step count measuring unit 104 configured to measure the step count based on the acceleration and the threshold value that has been determined by the threshold value determination unit 103. According to the above arrangement, it is possible to accurately measure the step count when the user is walking and when the user is running.

Further, in the step count measuring apparatus 1, the threshold value determination unit 102 determines a first threshold value (threshold value B) as a threshold value in the case where a local maximum value exceeds a predetermined value A, and determines a second threshold value (threshold value C) that is less than the first threshold value (threshold value B) as the threshold value in the case where the local maximum value is equal to or less than the predetermined value A. According to the above arrangement, the first threshold value (threshold value B) is determined as the threshold value in the case where the local maximum value exceeds the predetermined value A (i.e., when running), and the second threshold value (threshold value C) that is less than the first threshold value (threshold value B) is determined as the threshold value in the case where the local maximum value is equal to or less than the predetermined value A (i.e., when walking). Therefore, the step count while walking and the step count while running can be measured more accurately.

Further, in the step count measuring apparatus 1, the threshold value is determined after the local maximum value and the local minimum value have been both detected by the local maximum/minimum value detection unit 102. According to the above arrangement, the threshold value determination unit 103 determines the threshold value after the local maximum value and the local minimum value have been both detected by the local maximum/minimum value detection unit. Therefore, the step count while walking and the step count while running can be measured furthermore accurately.

Further, the local maximum/minimum value detection unit 102 of the step count measuring apparatus 1 detects the local maximum value and the local minimum value, and the step count measuring unit 104 measures the step count based on a difference between the local maximum value and the local minimum value detected by the local maximum/minimum value detection unit 102. According to the above arrangement, it is possible to measure the step count more accurately.

Further, in the step count measuring apparatus 1, the acceleration that is input to the local maximum/minimum value detection unit 102 is a sum of the squares of acceleration values in three axis directions including an X axis, a Y axis, and a Z axis that are orthogonal to each other. According to the above arrangement, compared with a case in which only acceleration(s) in one axis direction or two axis directions are used, the body movement of the user can be determined more accurately. As a result, it is possible to measure the step count more accurately.

Further, the step count measuring apparatus 1 includes an acceleration sensor that measures acceleration. According to the above arrangement, an acceleration sensor that measures acceleration is included. Therefore, it is not necessary to include a separate acceleration sensor. Further, compared with a gyro sensor, less power is consumed. Therefore, the above arrangement is preferable for a wearable device or a mobile device that is driven by an internal power supply such as a storage battery.

Further, a step count measuring program according to an embodiment of the present invention may realize the step count measuring apparatus 1, and may provide the same effects as the above step count measuring apparatus 1. According to the above arrangement, the threshold value determination unit determines the threshold value after one of the local maximum value and the local minimum value has been detected by the local maximum/minimum value detection unit. Therefore, compared with a case in which the threshold value is determined after the local maximum value and the local minimum value have been both detected, it is possible to determine the threshold value in a shorter time.

Second Embodiment

Next, a second embodiment of the present invention will be described. In the first embodiment, the threshold value is determined by determining whether the local maximum value detected by the local maximum/minimum value detection unit 102 exceeds the predetermined value A, after the local minimum value and the local maximum value have been detected by the local maximum/minimum value detection unit 102. In the second embodiment, the threshold value is determined by determining whether the local maximum value detected by the local maximum/minimum value detection unit 102 exceeds the predetermined value A after the local maximum value has been detected by the local maximum/minimum value detection unit 102, which will be described below.

Figure 6:
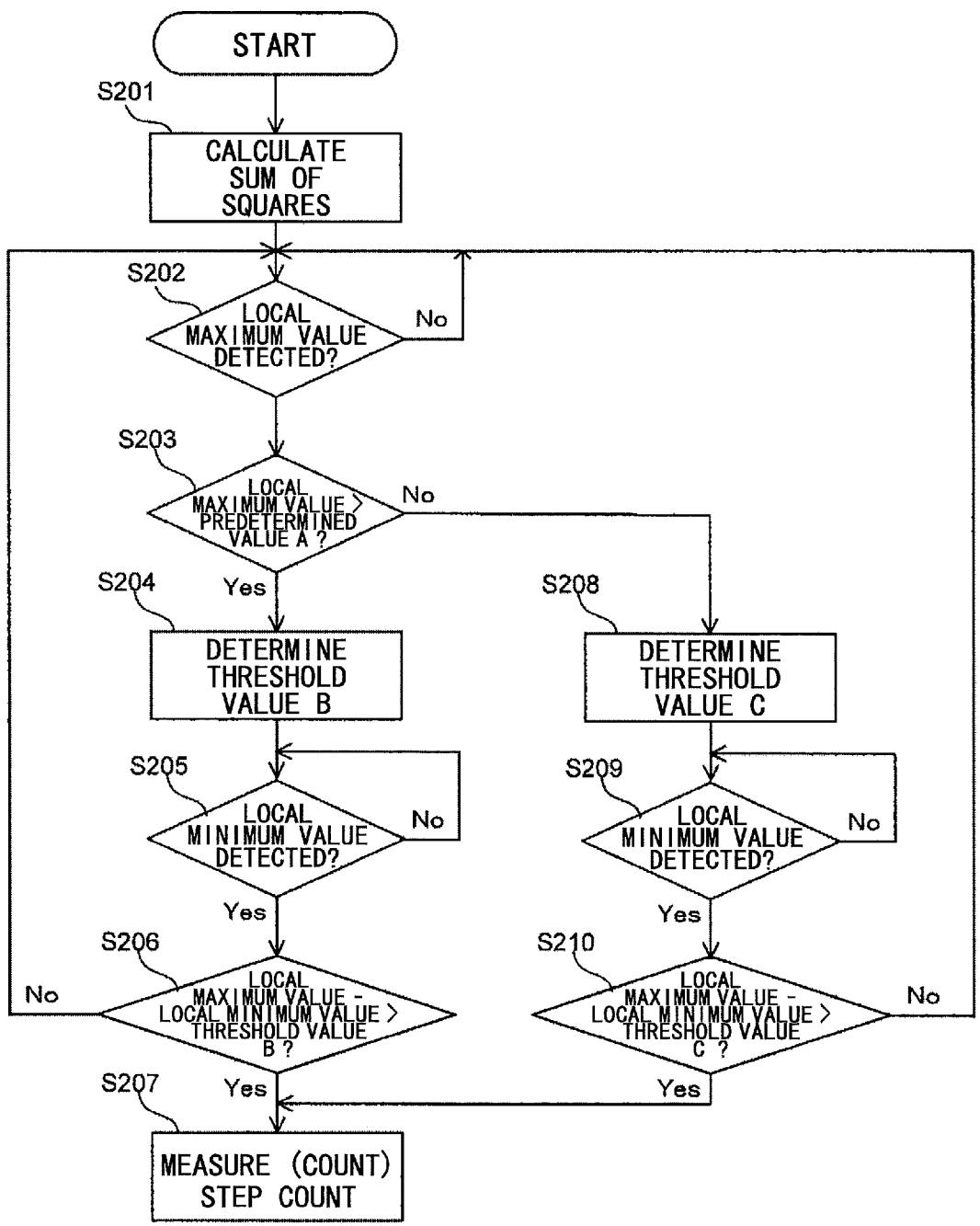
FIG. 6 is a flowchart illustrating operations of a step count measuring apparatus according to a second embodiment of the present invention.

FIG. 6 is a flowchart illustrating operations of a step count measuring apparatus 1 according to the second embodiment. In the following, referring to FIG. 1 through FIG. 4 and FIG. 6, operations of the step count measuring apparatus 1 according to the second embodiment will be described.

At first, after sampling the analog voltage signals in the X axis, Y axis, and Z axis, that are output from the acceleration sensor 2 at a predetermined sampling period, and converting the sampled analog voltage signals into digital data, the sum of squares calculation unit 101 calculates the square root of the sum of the squares of the respective acceleration values in the X axis, Y axis, and Z axis that have been converted to the digital data (S201).

Next, the local maximum/minimum value detection unit 102 performs sampling of the values output from the sum of squares calculation unit 101 during a predetermined time, and detects a local maximum value (the largest value) from the sampled values during the predetermined time (S202).

Next, the threshold value determination unit 103 determines whether the local maximum value detected by the local maximum/minimum value detection unit 102 exceeds a predetermined value A (S203). In the case where the local maximum value detected by the local maximum/minimum value detection unit 102 exceeds the predetermined value A (Yes in S203), the threshold value determination unit 103 determines that the user is running, and determines a threshold value B (first threshold value) as a threshold value to be used (S204).

Further, after detecting the local maximum value in S202, the local maximum/minimum value detection unit 102 continues to detect the local minimum value (S205). After calculating a difference between the local maximum value and the local minimum value that have been detected by the local maximum/minimum value detection unit 102, the step count measuring unit 104 determines whether the difference exceeds the threshold value B that has been determined by the threshold value determination unit 103 in step S204 (S206).

In the case where the difference exceeds the threshold value B (Yes in S206), one step is measured by the step count measuring unit 104 (S207). Further, in the case where the difference does not exceed the threshold value B (No in S206), no step is measured by the step count measuring unit 104.

Further, in the case where the local maximum value detected by the local maximum/minimum value detection unit 102 does not exceed the predetermined value A (No in S203), the threshold value determination unit 103 determines that the user is walking, and determines a threshold value C (second threshold value) as the threshold value to be used (S208).

Further, after detecting the local maximum value in S202, the local maximum/minimum value detection unit 102 continues to detect the local minimum value (S209). After calculating a difference between the local maximum value and the local minimum value that have been detected by the local maximum/minimum value detection unit 102, the step count measuring unit 104 determines whether the difference exceeds the threshold value C determined by the threshold value determination unit 103 in step S208 (S210). In the case of the difference exceeding the threshold value C (Yes in S210), one step is measured by the step count measuring unit 104 (S207). Further, in the case where the difference does not exceed the threshold value C (No in S210), no step is measured by the step count measuring unit 104.

In the second embodiment, the similar effects as the first embodiment can be obtained. Further, according to the second embodiment, the threshold value determination unit 103 determines the threshold value after the local maximum value has been detected by the local maximum/minimum detection unit 102. Therefore, the threshold value can be determined in a shorter time.

Other Embodiments

In the first embodiment and the second embodiment, the threshold value is determined by determining whether the local maximum value that has been detected by the local maximum/minimum value detection unit 102 exceeds the predetermined value A, which has been described above. However, the threshold value may be determined by determining whether an absolute value of the local minimum value exceeds a predetermined value D (a value different from the predetermined value A). Further, the threshold value may be determined by determining whether an absolute value of the local maximum value and an absolute value of the local minimum value exceed the predetermined values A and D, respectively.

Further, in the second embodiment, the threshold value determination unit 103 determines the threshold value after the local maximum value has been detected by the local maximum/minimum value detection unit 102. However, the threshold value determination unit 103 may determine the threshold value after the local minimum value has been detected by the local maximum/minimum value detection unit 102.

Further, in the second embodiment, after detecting the local minimum value in S202, whether or not an absolute value of the local minimum value exceeds the predetermined value D may be determined in S203. In this case, in steps S205 and S209, the local maximum value is detected.

Further, in a step count measuring apparatus 1 according to the first and second embodiment, whether the user is walking or running is determined by using a square root of the sum of the squares of the acceleration values in the X axis, Y axis, and Z axis output from the acceleration sensor 2. However, whether the user is walking or running may be determined by using at least one of the values with respect to the X axis, Y axis, and Z axis output from the acceleration sensor 2.

DESCRIPTION OF THE REFERENCE NUMERALS

1 step count measuring apparatus
2 acceleration sensor
101 sum of squares calculation unit
102 local maximum/minimum detection unit
103 threshold value determination unit
104 step count measuring unit
105 memory unit

What is claimed is:

1. A step count measuring apparatus that measures a step count based on a degree of acceleration data, the step count measuring apparatus comprising:
    an acceleration sensor that measures the acceleration data; and
    a processor, wherein the processor
    detects at least one of a local maximum value and a local minimum value of the acceleration data in a predetermined time,
    determines a threshold value based on the at least one of the local maximum value and the local minimum value that has been detected by the processor,
    measures the step count based on the acceleration data and the threshold value that has been determined by the processor, and wherein
    the processor determines a first threshold value as the threshold value in the case where the at least one of the local maximum value and the local minimum value exceeds a predetermined value, and determines, as the threshold value, a second threshold value that is less than the first threshold value in the case where the at least one of the local maximum value and the local minimum value is equal to or less than the predetermined value.

2. The step count measuring apparatus according to claim 1, wherein the processor determines the threshold value after the local maximum value and the local minimum value have been both detected by the processor.

3. The step count measuring apparatus according to claim 1, wherein the processor determines the threshold value after one of the local maximum value and the local minimum value has been detected by the processor.

4. The step count measuring apparatus according to claim 1, wherein
    the processor measures the step count based on a difference between the local maximum value and the local minimum value that has been detected by processor.

5. The step count measuring apparatus according to claim 1, wherein the acceleration data that is input to the processor is a sum of the squares of acceleration values in three axes including a X axis, a Y axis, and a Z axis that are orthogonal to each other.

6. A non-transitory computer readable recording medium that includes a step count measuring program used for measuring a step count based on a degree of acceleration data, the step count measuring program causes a computer to:
    measure the acceleration data:
    detect at least one of a local maximum value and a local minimum value of the acceleration data in a predetermined time;
    determine a threshold value based on the at least one of the local maximum value and the local minimum value that has been detected by the detecting;
    measure the step count based on the acceleration data and the threshold value that has been determined by the determining;
    determine a first threshold value as the threshold value in the case where the at least one of the local maximum value and the local minimum value exceeds a predetermined value; and
    determine, as the threshold value, a second threshold value that is less than the first threshold value in the case where the at least one of the local maximum value and the local minimum value is equal to or less than the predetermined value.

\* \* \* \* \*